US011071535B2

(12) United States Patent
Gittard et al.

(10) Patent No.: US 11,071,535 B2
(45) Date of Patent: Jul. 27, 2021

(54) VASCULAR ANCHORING INTRODUCER SHEATH

(71) Applicant: Muffin Incorporated, West Lafayette, IN (US)

(72) Inventors: Shaun Davis Gittard, Winston-Salem, NC (US); Gregory James Hardy, Asheville, NC (US); John C. Sigmon, Jr., Winston-Salem, NC (US); Jeremy T. Newkirk, West Lafayette, IN (US); William J. Havel, West Lafayette, IN (US); Neal E. Fearnot, West Lafayette, IN (US); Toby Rogers, Washington, DC (US); Kanishka Ratnayaka, Bethesda, MD (US); Robert L. Lederman, Chevy Chase, MD (US)

(73) Assignees: Muffin Incorporated, West Lafayette, IN (US); National Institutes of Health, DHHS, Bethesda, MD (US)

( * ) Notice: Subject to any disclaimer, the term of this patent is extended or adjusted under 35 U.S.C. 154(b) by 195 days.

(21) Appl. No.: 16/394,182

(22) Filed: Apr. 25, 2019

(65) Prior Publication Data

US 2019/0247035 A1 Aug. 15, 2019

Related U.S. Application Data

(63) Continuation of application No. PCT/US2017/058245, filed on Oct. 25, 2017.
(Continued)

(51) Int. Cl.
*A61B 17/02* (2006.01)
*A61M 25/00* (2006.01)
(Continued)

(52) U.S. Cl.
CPC .......... *A61B 17/0218* (2013.01); *A61B 90/39* (2016.02); *A61M 25/0041* (2013.01); *A61M 25/0045* (2013.01); *A61M 25/10* (2013.01); *A61B 2017/00247* (2013.01); *A61B 2017/00557* (2013.01); *A61B 2017/00845* (2013.01); *A61B 2017/00955* (2013.01);
(Continued)

(58) Field of Classification Search
CPC ..... A61B 17/02; A61B 17/0218; A61B 90/00; A61B 90/39
See application file for complete search history.

(56) References Cited

U.S. PATENT DOCUMENTS

| 5,429,605 A | 7/1995 | Richling et al. |
| 2002/0058910 A1 | 5/2002 | Hermann et al. |

(Continued)

OTHER PUBLICATIONS

International Application No. PCT/US2017/058245 International Search Report and Written Opinion, dated Jan. 30, 2018.

*Primary Examiner* — Christopher J Beccia
(74) *Attorney, Agent, or Firm* — Woodard, Emhardt et al.

(57) ABSTRACT

Among other things, there is disclosed structure and methods for maintaining access to a location in the body while reducing or eliminating the potential for pulling an access device (e.g. a catheter) back through an opening. An introducer sheath includes a distal indented portion and a balloon, so that once placed in a desired location through tissue, the balloon can be inflated to anchor the sheath against retraction. In particular embodiments, structure and methods for accessing the pericardial cavity via the right atrial appendage are shown.

12 Claims, 3 Drawing Sheets

Related U.S. Application Data

(60) Provisional application No. 62/412,646, filed on Oct. 25, 2016.

(51) Int. Cl.
*A61M 25/10* (2013.01)
*A61B 90/00* (2016.01)
A61B 17/34 (2006.01)
A61M 25/06 (2006.01)
A61B 17/00 (2006.01)
A61M 25/01 (2006.01)

(52) U.S. Cl.
CPC ............... *A61B 2017/0225* (2013.01); *A61B 2017/0237* (2013.01); *A61B 2017/3486* (2013.01); *A61B 2090/3925* (2016.02); *A61B 2090/3966* (2016.02); *A61M 25/0052* (2013.01); *A61M 25/0054* (2013.01); *A61M 25/0108* (2013.01); *A61M 25/0662* (2013.01); *A61M 2025/0047* (2013.01); *A61M 2025/1079* (2013.01); *A61M 2025/1093* (2013.01)

(56) References Cited

U.S. PATENT DOCUMENTS

2007/0255207 A1 11/2007 Hangai et al.
2008/0243081 A1 10/2008 Nance et al.

VASCULAR ANCHORING INTRODUCER SHEATH

The present disclosure concerns devices for safely anchoring with respect to tissue and allowing introduction of other devices into a desired treatment location through them. In particular, the disclosure concerns an introducer able to be inserted through and anchored with respect to tissue such as the right atrial appendage. This invention was created in the performance of a Cooperative Research and Development Agreement with the National Institutes of Health, an Agency of the Department of Health and Human Services. The Government of the United States has certain rights in this invention. This application is a continuation of PCT/US2017/058245, filed on Oct. 25, 2017 which claims the benefit of U.S. Provisional Application Ser. No. 62/412,646, filed on Oct. 25, 2016, which is incorporated herein by reference in its entirety.

BACKGROUND

There are numerous applications in which a vascular introducer sheath is passed through tissue and inadvertent pullback would he undesirable. For example, a common approach for accessing the left atrium of the heart is to enter the right atrium via the venous system and puncture through the interatrial septum to reach the left atrium. Once across the septum, if the introducer inadvertently is pulled back across the septum into the right atrium, puncturing the septum must be repeated which causes additional trauma. In another example, a way of accessing the pericardium from within the heart is by puncturing out of the right atrial appendage into the pericardium. Inadvertently pulling the introducer sheath back into the heart could cause pericardial tamponade, which can lead to death.

When accessing the vascular system via a percutaneous puncture, bleeding or a hematoma can occur if the introducer sheath is inadvertently pulled out of the blood vessel. When crossing from one blood vessel to another by exiting the bloodstream (e.g. from the vena cava to the aorta), bleeding or a hematoma can occur if the introducer sheath is inadvertently pulled out of the blood vessel.

Currently available devices do not have an anchoring feature particularly suitable to the sensitive tissues of the heart. A number of devices have been proposed to access cardiac tissue or the pericardium by punching or other insertion through cardiac or adjacent tissues. Such devices allow access, but commonly lack any structure for holding the device with respect to the tissue through which the device is placed because such anchoring is not required or desired. For an access device that allows medication or other fluid to flow into a cavity, as one example, an anchor is not required. An anchor is also undesirable for an introducer where the opening or tissue through which the introducer is placed is in a sensitive location, and where expansion or damage to the hole or tissue must be avoided.

The present disclosure provides a device that resolves such issues.

SUMMARY

Among other things, there is disclosed an introducer sheath for insertion through the right atrial appendage into the pericardial cavity. Embodiments of the sheath can include an inner lubricious layer defining an internal lumen extending along a longitudinal axis of the sheath from a proximal end to a distal end of the sheath, an outer heat-settable layer surrounding the inner layer and extending from the proximal end to the distal end, and a coil core fixed between the inner layer and the outer layer. The coil core may extend through at least part of a proximal portion of the sheath and at least part of a medial curved portion of the sheath but not into a linear distal portion of the sheath which includes the distal end in particular embodiments.

The linear distal portion may have a circumference around the longitudinal axis, and include an indented portion around the entire circumference, the indented portion having proximal and distal edges an outer diameter less than a maximum outer diameter of the linear distal portion. A balloon is in the indented portion, the balloon having a deflated condition in which the balloon does not extend past either of the edges or the maximum outer diameter of the linear distal portion, and an inflated condition in which the balloon extends coaxially past the maximum outer diameter of the linear distal portion around the circumference of the linear distal portion. In the inflated condition, the balloon has a surface facing proximally that is angled with respect to the longitudinal axis at an angle between and including 60 to 90 degrees.

In certain embodiments, the internal lumen has a constant inner diameter through the proximal, medial and distal portions of the sheath. The sheath can also include at least one marker that abuts the proximal edge of the indented portion, the marker being at least one of radiopaque and echogenic. In particular the marker may be proximal of a proximal-most part of the balloon. A fluid lumen extends to an opening in the indented portion, whereby a fluid may be forced through to inflate the balloon and may be withdrawn to deflate the balloon. Particular embodiments use polytetrafluoroethylene (PTFE) for the inner layer, and/or PEBAX for the outer layer. The outer layer may be heat-set to a desired shape following attachment of the inner and outer layers to each other.

Methods, including methods of accessing a pericardial cavity of a patient via a right atrial appendage of the patient with an introducer sheath, are also disclosed. Such methods can include inserting the introducer sheath into the inferior vena cava of the patient, the introducer sheath having a curved medial portion and a linear distal portion, the linear distal portion including an indented portion around the entire circumference and a balloon in a deflated condition within the indented portion so that no part of the balloon extends beyond a maximum outer diameter of the linear distal portion or outside of the indented portion. The sheath can be moved to the right atrium of the heart of the patient to a position adjacent the right atrial appendage, and passed through the right atrial appendage to the pericardial cavity so that the indented portion is within the pericardial cavity. The balloon can be inflated within the pericardial cavity, so that the inflating does not enlarge a hole through the right atrial appendage through which the sheath passes, and the inflated balloon can be engaged with tissue of the right atrial appendage that faces the pericardial cavity.

In particular examples, the introducer sheath is an embodiment described herein. The sheath may be imaged when it extends through the right atrial appendage, and confirming that a marker abutting a proximal edge of an indented or balloon section is beyond the tissue of the right atrial appendage before performing the inflating step. A dilator may be within and extending from the sheath, and the passing step may include dilating a hole through the right atrial appendage with the dilator. In certain embodiments, the dilator and sheath are placed and moved over a wire of a wire guide, which has already been passed through the right atrial appendage and into the pericardial cavity or space. The dilator may have a very gradual taper to allow gentle dilation of the right atrial appendage, such as a taper length of about 5 centimeters. The dilator may also lock into or with respect to the sheath during delivery, so that the dilator and sheath move in unison during the insertion procedure.

One or more devices may be passed through the sheath and into the pericardial cavity for use in a treatment procedure after the engaging step, and while the balloon is inflated and engaged with tissue of the right atrial appendage. In particular examples, the device(s) may include a belt for placement in the atrioventricular groove as a treatment for tricuspid valve regurgitation. The balloon may be deflated so that the balloon collapses to a condition within the indented portion so that no part of the balloon extends beyond a maximum outer diameter of a distal portion of the sheath or outside of the indented portion of the sheath. Further, a disengaging can occur between the engaging and the deflating, wherein the disengaging includes moving the sheath with respect to the right atrial appendage to move the balloon away from tissue of the right atrial appendage that faces the pericardial cavity.

The disclosed devices and methods prevent inadvertent pullback of an introducer catheter within the bloodstream or cardiac tissues. In certain embodiments, a tubular sheath has a balloon mounted along the exterior of its shaft, e.g. in an indented portion. The sheath is sized for introduction through the vascular system and placement at a desired location in the body. It is also sized so that a medical device can be passed through it to the desired location. In one example, the introducer sheath is sized such that 14 French devices can pass through it. At the proximal end is a port that communicates with the inner diameter of the catheter. A second port on the proximal end is in fluid communication with the balloon, such that it can be used to inflate or deflate the balloon. Fluid communication between the second port and balloon can be achieved either via a second lumen in the catheter (multi-lumen catheter system) or a sleeve which is placed around the sheath or inner lumen (coaxial system). More generally, devices for maintaining access after exiting a vascular or cardiac wall include a catheter or sheath having a distal end and an outer diameter, and further including a bonded balloon attached to the distal end, wherein the balloon inflates to a diameter that is at least 2 times the diameter of the access catheter's outer diameter, and preferably at least 3 times. Ports on the proximal end can be provided for device insertion, contrast injection, and/or balloon inflation while maintaining a seal to prevent blood loss out of the proximal end of the catheter or sheath.

Exemplary methods include passing a sheath from the inferior vena cava via the right atrium to the right atrial appendage. The sheath is passed through the wall of the right atrial appendage such that the distal end of the sheath is in the pericardial cavity. The inflated balloon at the distal end prevents the sheath from being pulled back into the heart. More generally, methods are disclosed for maintaining access after exiting a vascular or cardiac wall through inflation of a balloon that is attached to the access sheath or tube so that the balloon inflates outside of the wall to prevent premature pullback and subsequent loss of access. In particular, methods for achieving and maintain pericardial access, so that devices and tools can be delivered inside the pericardium safely without losing access prematurely, are disclosed.

DESCRIPTION OF THE ILLUSTRATED EMBODIMENTS

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the disclosure is thereby intended. Any alterations and further modifications in the described embodiments and any further applications of the principles of the present disclosure as described herein are contemplated as would normally occur to one skilled in the art to which the disclosure relates.

Referring now generally to the drawings, there is shown an embodiment of an introducer sheath 20, which is adapted for use in the body to allow other devices (such as catheters, diagnostic devices, or treatment devices) to travel through sheath 20 to a desired location in the body. As an example, sheath 20 is preferably able to be inserted into the vasculature of a patient, such as into the inferior vena cava (IVC), moved to a location for diagnosis or treatment such as the heart, and anchored in or through tissue at or near the location. Another device, such as a dilator or treatment device, is passed through and out of a distal end of sheath 20, so that the device extends through the tissue with respect to which sheath 20 is anchored.

Sheath 20 in the illustrated embodiment is a multi-layer device, having an inner layer 22 surrounding a central lumen 24, an outer layer 26, and a coil core 28 that is between and/or at least partially embedded in one or both of inner layer 22 and outer layer 26. Sheath 20 has a proximal (i.e. closer to the user or operator of sheath 20) portion 32, a medial curved portion 34, and a distal (i.e. farther away from the user or operator of sheath 20) portion 36.

Inner layer 22 in a particular embodiment is of a highly lubricious substance, for example PTFE (also known as Teflon), defining a lumen 24 that is sized to permit passage of a dilator D to assist in placement of sheath 20, as well as to permit passage of additional tools or structures for treatment of tissue, as will be discussed further below. The diameter of lumen 24 is constant in the illustrated embodiment through proximal, medial and distal portions 32, 34, 36, and may be 9 French, 11 French or 13 French as particular examples. The use of PTFE or similarly lubricious material for the inner layer is preferred so as to easily pass dilator D or other devices, even in an environment like the body (e.g. the vasculature).

Outer layer 26 surrounds inner layer 22 to form an outermost surface 40 in a particular embodiment is of a heat-settable and soft or low-friction substance, for example PEBAX (polyether block amide). Outer layer 26 may be heat-set into a desired shape, including cylindrical or oval, and is easily formed into the surfaces described below with respect to distal portion 36. In particular embodiments, a cylindrical shape will make turning sheath 20 by application of torque easier, and in other embodiments an oval shape can make anchoring with respect to tissue more secure. It will be understood that sheath 20 may have a single outer shape or configuration, e.g. cylindrical throughout, or may have more than one outer shape or configuration, e.g. cylindrical in proximal and/or medial portions 32, 34, and oval in all or part of distal portion 36.

Figure 1:
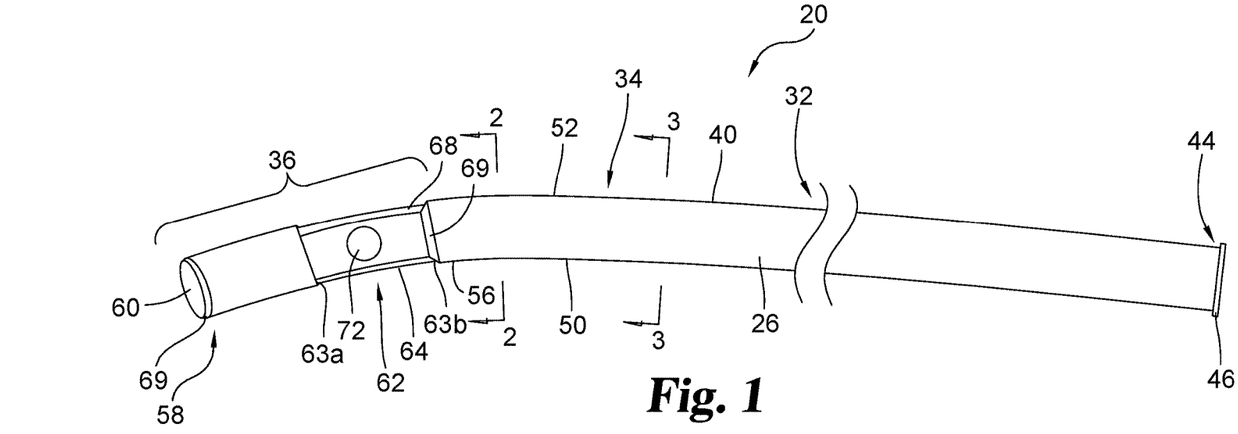
FIG. 1 is a side plan view of an embodiment of an introducer sheath as disclosed herein
Figure 2:
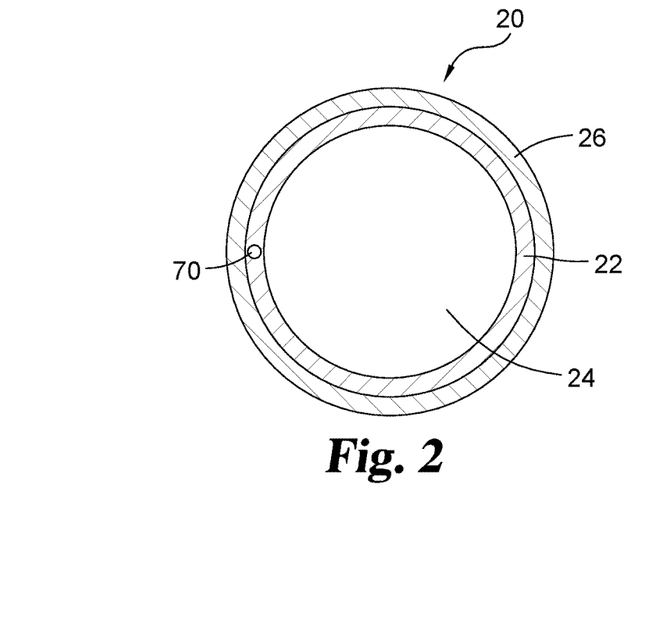
FIG. 2 is a cross-sectional view of the embodiment of FIG. 1, taken along the lines II-II in FIG. 1.
Figure 3:
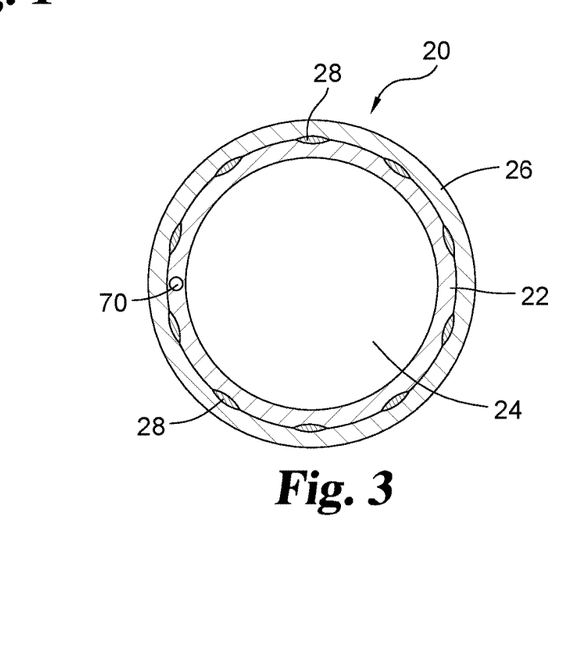
FIG. 3 is a cross-sectional view of the embodiment of FIG. 1, taken along the lines III-III in FIG. 1.

Coil core 28 is between and/or at least partially embedded in one or both of layers 24, 26 in the illustrated embodiment. Core 28 is a coiled filament or wire in a particular embodiment, of a sturdy material such as biocompatible metals or plastics. Core 28 provides sturdiness to sheath 20 to allow torquing for turning of sheath 20 around a longitudinal axis and resist or prevent kinking, while its windings maintain flexibility in sheath 20 so that it can be moved through the vasculature or other paths through the body. The filament or wire of core 28 may be cylindrical in cross section, or rectangular in cross section (e.g. a flat wire, indicated in FIG. 3), and core 28 may include a single wound filament or wire, or two or more filaments or wires wound around each other or around a common longitudinal axis. The illustrated embodiment shows coil core 28 partially embedded in both layers 22 and 26, i.e. a part of the windings of core 28 is within the largest outer diameter of inner layer 22 and beyond the smallest inner diameter of outer layer 26. It will be understood that core 28 may be wound around the outer diameter of inner layer 22, and the outer layer 26 molded or otherwise formed around core 28 and layer 22, so that core 28 is embedded at least partially in outer layer 26. Alternatively, core 28 may remain between the outer diameter of inner layer 22 and the inner diameter of outer layer 26, and not be embedded in either layer.

Proximal portion 32 of sheath 20 is generally straight in the illustrated embodiment, with sufficient flexibility to permit maneuvering through the vasculature (e.g. through the IVC to the heart). Proximal portion 32 includes a portion of each of inner layer 22, outer layer 26 and coil core 28. A proximal end 44 may include a hub or locking mechanism 46 that engages with or locks to a handle or other device to enable moving, turning or otherwise maneuvering sheath 20, either by itself or in conjunction with another related device. As a particular example, dilator D may include a hub (not shown) that is compatible with mechanism 46 of sheath 20, so that when dilator D is in a position to extend from distal portion 36 of sheath 20, the hub of dilator D engages and/or locks with mechanism 46. In this way, sheath 20 and dilator D can be moved together, e.g. with one handle or control, without the risk of one moving further or in a different way than the other.

Medial portion 34 is curved in this embodiment, so that there is a concave side 50 and a convex side 52 on opposite sides of the longitudinal axis. In the illustrated embodiment, the concave curvature of side 50 extends around about 20-40 degrees of arc, although it will be understood that the curvature could extend through greater or lesser amounts of arc depending on the particular use or area of the body in which sheath 20 is to be used. The exemplary embodiment can be used in placing sheath through the right atrial appendage to access the pericardium, as will be explained further below. Medial portion includes inner layer 22 with its constant diameter lumen 24, core coil 28 and outer layer 26. In particular embodiments, the curvature of medial portion 34 is formed and maintained by initially forming or imbuing one or both of core 28 and outer layer 26 with the curvature. In this way, when sheath 20 is assembled, as by forcing a curved core 28 over inner layer 22, the curvature of core 28 is imparted to layer 22. Similarly, if outer layer 26 is a heat-settable material, it may be set after sheath 20 is assembled to the desired curvature, so that outer layer 26 forces its set curvature onto core 28 and layer 22.

Distal portion 36 adjoins curved medial portion 34, and in the illustrated embodiment is straight linear and has a joining part 56 that connects to medial portion 34, an end 58 with an opening 60 that communicates with lumen 24, and an indented portion 62 (with edges 63a, 63b) between part 56 and end 58. It has been found preferable to minimize the length from indented portion 62 to the tip of end 58 (i.e. at opening 60), with examples being 6 millimeters or less. Straight distal portion 36 includes outer layer 26 and inner layer 22, but does not include coil core 28, so that distal portion 36 is more flexible and/or softer than medial portion 34 and proximal portion 32. Joining part 56 has an outer diameter (of outer layer 26) that is the same as the outer diameter of medial portion 34 and proximal portion 32. End 58 reduces in outer diameter from an outer diameter adjacent indented portion 62 that is the same as the outer diameter of part 56, to an outer diameter at opening 60 that is minimally larger than the diameter of lumen 24. In this way, opening 60 has a lip or edge that is about the same as the outer diameter of a dilator D that passes through opening 60, and presents little or no step between dilator D and the outer surface of end 58, thereby reducing or eliminating the risk of trauma to tissue as sheath 20 moves (with dilator D) through the tissue. The reduction in outer diameter may be a result of reducing the thickness of outer layer 26, the thickness of inner layer 22, or both.

Indented portion 62, as already noted, is between end 58 and part 56, and has an outer diameter that is less than that of part 56, medial portion 34 and proximal portion 32. A balloon 64 is within part or all of portion 62 in the illustrated embodiment, so that when balloon 64 is not inflated it is at or below the maximum outer diameter of end 58 (i.e. the outer diameter of joining part 56, which is the same as the outer diameter of medial portion 34 and proximal portion 32 of sheath 20), and fully inside of edges 63a, 63b. In this way, when uninflated balloon 64 does not present a larger profile than the rest of sheath 20.

Balloon 64, in the illustrated embodiment, is a layer of expandable material fixed in an airtight fashion to the outer surface of indented portion 62. Balloon 64 extends around the entire circumference of sheath 20, and in particular embodiments has a constant length L as measured along the longitudinal axis of sheath 20. Fluid (e.g. air or other gas, or saline or other liquid) is forced between balloon layer 64 and the outer surface of indented portion 62 to expand balloon 64 and a volume enclosed by balloon layer 64 and the outer surface of indented portion 62. Alternatively, balloon 64 may be an annular balloon fixed within indented portion 62, so that forcing fluid into balloon 64 results in expansion of balloon 64 and a volume enclosed by balloon 64, but not contacting indented surface 62. In either case, or with other configurations of balloon 64, a proximal edge 68 of balloon 64 is within the straight distal portion 36 of sheath 20, and inflates coaxially with respect to the longitudinal axis of sheath 20. That is, balloon 64 expands all the way around the circumference of indented portion 62. Preferably the expansion is to the same or approximately the same extent at all locations around the circumference, e.g. the expanded extent of balloon 64 is at least approximately the same distance from the longitudinal axis of sheath 20 all the way around the outermost diameter of balloon 64. In particular embodiments, the outermost edges of balloon 64 in its expanded condition have a diameter that is at least 2 times the outer diameter of sheath 20 (e.g. maximum outer diameter of distal section 36), and preferably at least 3 times that diameter.

In particular embodiments, balloon 64 presents a surface 68 generally facing proximally (e.g. toward medial portion 34 and/or proximal portion 32 of sheath 20) when balloon is inflated. Surface 68 in the illustrated embodiment has an angle of approximately 90 degrees with respect to the longitudinal axis of sheath 20, along at least a portion of surface 68, such as the portion closest to the outer surface of sheath 20 in or adjacent to indented portion 62. In other embodiments, the angle of surface 68 (or at least the closest portion to the outer surface of sheath 20) with respect to the longitudinal axis is between or including 85 and 90 degrees, between and including 75 and 90 degrees, and/or between and including 60 and 90 degrees (e.g. an angle of at least 60 degrees with respect to the longitudinal axis of sheath 20. Surface 68, as will be explained further below, is adapted to engage tissue through which sheath 20 extends, to prevent sheath 20 from moving back through the tissue. Sheath 20 can be retracted through such tissue when balloon 64 is deflated.

One or more markers 69 may be placed at the base of indented portion 62. In the illustrated embodiment, a band of biocompatible metal is placed around the outside of outer layer 26 of sheath 20 and abutting (e.g. touching) the proximal end of indented portion 62. Such a band is radiopaque and reflects ultrasound. It will be understood that other embodiments of marker(s) 69 may be of other radiopaque and/or echogenic material, or capable of being imaged via other types of imaging systems. It will also be understood that marker(s) 69 may be at particular points rather than formed as a band, or in other formations so as to be easily seen from a number of directions under imaging. The placement of marker(s) 69 is to show at least approximately where surface 68 will be when balloon 64 is inflated. Dilator D is preferably more radiopaque or echogenic than sheath 20 (or particularly marker 69) so as to provide a contrast with sheath 20 during imaging. In the illustrated embodiment, one or more marker(s) 69 are also placed at the tip of end 58, adjacent opening 60, so as to be able to show the operator when the tip is through the RAA tissue, on entry or on later retraction at the end of a procedure. Marker(s) 69 are preferably more radiopaque or echogenic than dilator D so that marker(s) 69 can be easily seen when dilator D is within and being used with sheath 20.

An inflation channel extends through or along sheath 20 to balloon 64. In a particular embodiment, an inflation lumen 70 is along lumen 24 and extends to an opening 72 in indented portion 62 and under or within material of balloon 64. Lumen 70 and lumen 24 may be separate lumens in sheath 20, as in a multi-lumen catheter, or may be coaxial within sheath 20 as in a coaxial catheter. In other embodiments, inflation lumen 70 may be along the exterior of sheath 20 or through one or both of layers 22, 26. Lumen 70 is connected to a source of fluid and/or pressure (not shown), e.g. a syringe), so that fluid (e.g. air or saline) can be forced into or behind balloon 64 to inflate balloon 64. Such a source may also be used to withdraw fluid or pressure to deflate balloon 64 when desired. In particular embodiments, additional lumen(s) and corresponding communicating opening(s) or port(s) in proximal portion 32 and distal portion 36 may be provided for passage of contrast medium, medications, or other fluids. For example, such port(s) or opening(s) for inflation lumen 70 and/or passage of other fluids can be located at or near huh 46 facing in the direction that medial curved portion 34 curves toward, i.e. on the side of hub 46 that corresponds or is longitudinally aligned with concave side 50. In such embodiments, opening 72 (and other opening(s) for other fluids) will also be on the side of distal portion 36 that corresponds or is longitudinally aligned with concave side 50.

Use of sheath 20 will now be described, in the particular context of placement through the right atrial appendage (RAA) during placement of a belt or other device around the heart in treating tricuspid valve regurgitation (TR). It will be understood that embodiments of sheath 20 could be used in any of a number of internal diagnostic or treatment procedures.

Figure 4:
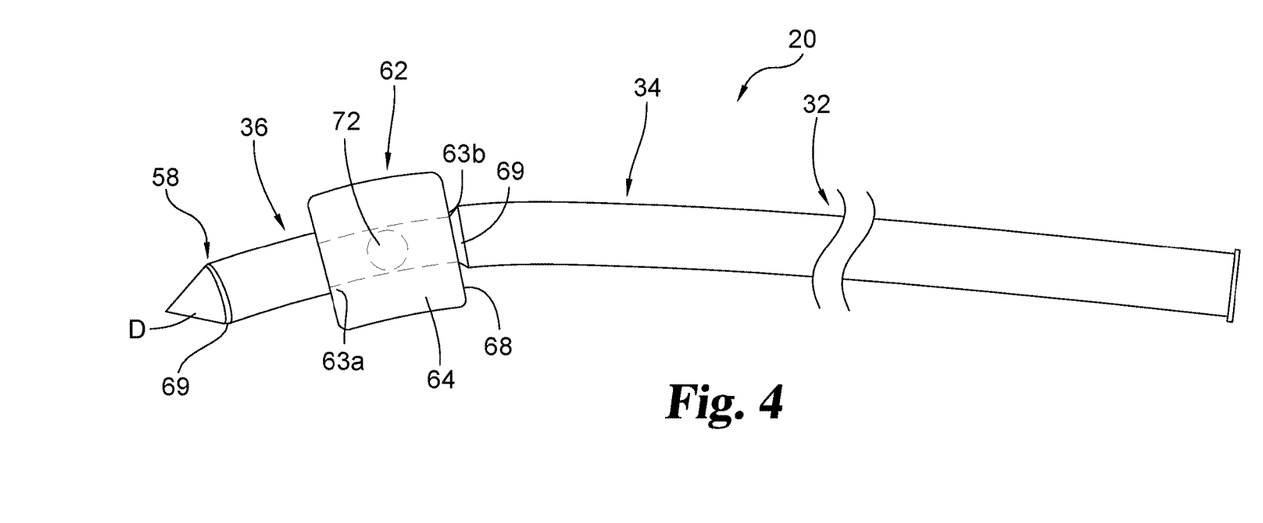
FIG. 4 is a side plan view of the embodiment of FIG. 1 in an inflated condition.

With balloon 64 deflated, and therefore within or even with the maximum outer diameter of sheath 20 in distal portion 36, sheath 20 is inserted into the body. In the embodiment illustrated in FIG. 4, a dilator D is shown so as to make and/or dilate a hole through the RAA, which has a forward surface that corresponds with the tip of end 58 of distal portion 36 of sheath 20. It will be understood that dilator D may be in the illustrated position with respect to sheath 20 when sheath 20 is inserted into the body, or may be passed through sheath 20 to the illustrated position after sheath 20 is inserted, e.g. just before moving sheath 20 through the tissue of the RAA and into the pericardial cavity.

Insertion of sheath 20 may be performed over a previously-placed wire of a wire guide as is known, e.g. one previously placed through the vasculature, right atrium, and tissue of the right atrial appendage to the pericardial cavity or space. In a particular embodiment, sheath 20 is inserted into the venous vasculature (e.g. into an iliac vein or the inferior vena cava (IVC)). If not initially inserted into the IVC, then sheath 20 is moved to and through the IVC, into the right atrium of the heart and to a location adjacent the RAA. Previously, access to the right atrium has been accomplished from a superior position, such as the jugular vein. However, it has been found that an inferior approach, through the IVC to the right atrium, has significant advantages in terms of patient comfort and care, ease of guidance, movement to and through the atrium and the RAA, and passage of treatment devices through sheath 20.

Figure 5:
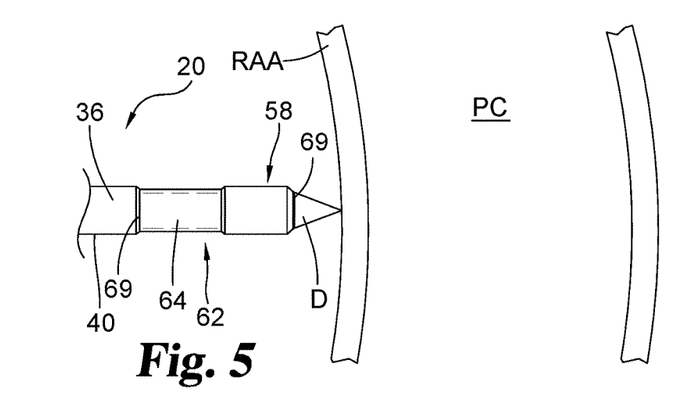
FIGS. 5-7 are side plan views of the embodiment of FIG. 1 in use.
Figure 6:
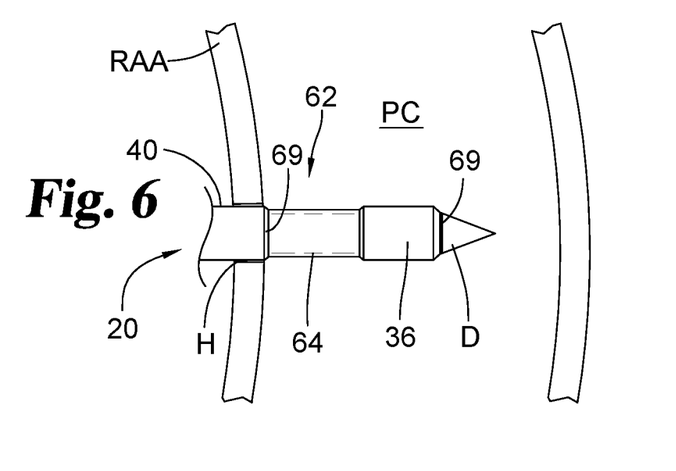
Figure 7:
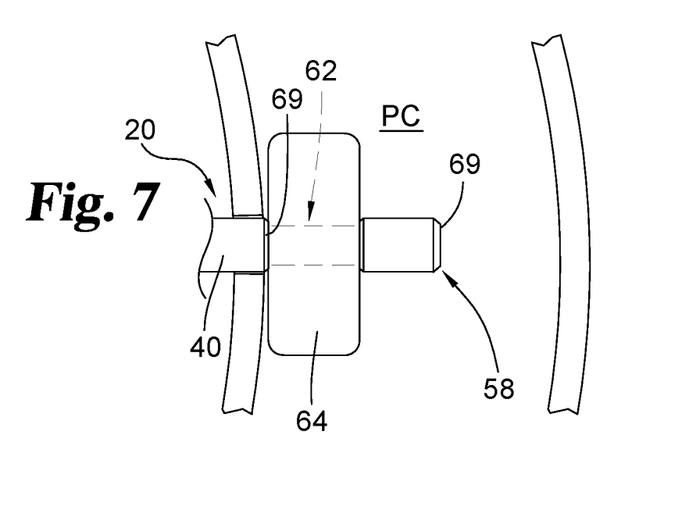

With sheath 20 (and dilator D in this embodiment) adjacent the RAA, as seen in FIG. 5, direction of dilator D and sheath 20 through hole H and into the pericardial cavity PC occurs (FIG. 6-7). Hole H may have been made previously, e.g. by a guiding wire such as one along which sheath 20 is moved or other tool, or may be made by dilator D or a tool passed along sheath 20. Sheath 20 with dilator D is moved so that dilator D engages RAA tissue at hole H, and is moved through the tissue so as to dilate hole H. The tissue around hole H engages the outside of dilator D and slides onto and around distal portion 36 of sheath 20, so that little or no leakage of fluid from the pericardial cavity into the RAA occurs. It will be understood that dilator D could be extended from sheath 20 (e.g. leaving sheath 20 stationary) and through the RAA tissue, and then sheath 20 may be advanced over dilator D and through hole H. In embodiments in which sheath 20 includes marker(s) 69, sheath 20 can be imaged (by x-ray, ultrasound, or other imaging system) to see where marker(s) 69 are with respect to the RAA tissue through which sheath 20 extends. When marker(s) 69 are seen to be past or clear of the RAA tissue (i.e. in the pericardial cavity or to the pericardial side of the RAA tissue), the operator stops advancing sheath 20.

When sheath 20 is fully advanced, i.e. balloon 64 and/or indented portion 62 is beyond the pericardial side of the RAA tissue (as may be indicated by marker(s) 69), the operator inflates balloon 64. Inflation should not occur prior to balloon 64 passing fully through hole H, so that hole H is not widened, with potential damage to the RAA and other complications. As noted above, balloon 64 inflates coaxially, around the entire circumference of sheath 20. When inflated, surface 68 of balloon 64 faces hole H and the pericardial side of the RAA tissue. Inflation of balloon 64 may engage surface 68 with tissue of the RAA around hole H directly, or the operator may need to retract sheath 20 only to the point that surface 68 firmly engages the RAA tissue. At this point, balloon 64 acts as an anchor against further retraction of sheath 20. Outer surface 40, preferably of distal portion 36 of sheath 20 adjacent and proximal of indented portion 62, is through and engaging the sides of hole H, and balloon surface 68 engages the pericardial side of the RAA.

It is noted that the straight, linear nature of distal portion 36 is advantageous over ends of catheters or other tubes that curve or curl in such methods. The linear distal portion 36 provides an even surface for balloon 64 to expand coaxially. It will also provide a better, more flush fit with hole H through the RAA, to minimize or eliminate leakage between sheath 20 and the RAA tissue, and an easier placement through that tissue. Further, when a curved catheter is deformed to pass through the RAA tissue a tendency to revert to the original curved form is created, which stress contributes to the potential for retraction. That stress is eliminated with the linear, straight section 36 of sheath 20 that passes through the RAA tissue.

With sheath 20 anchored against retraction through hole H, by balloon 64, dilator D may be retracted through sheath 20. Other tools or treatment structure may be passed through lumen 24 of sheath 20 and into the pericardial cavity. In the example of treatment of TR, a belt (not shown) is passed through sheath 20 and maneuvered around the heart so that the belt engages the atrioventricular (AV) groove. Additional structure may tighten the belt and hold it in place as may be desired.

Once the treatment is completed, and any tools or other structure to be withdrawn from the pericardial cavity and heart tissue has been retracted through sheath 20, sheath 20 itself is removed. Balloon 64 is deflated, so that balloon 64 returns into indented portion 62 of sheath 20, and preferably within or even with the adjacent outer diameter of proximal portion 32 of sheath 20. The operator may first move sheath 20 forward to disengage balloon surface 68 from the tissue of the RAA, if desired or necessary, so as to ensure that deflation of balloon 64 does not deleteriously affect the RAA tissue. With balloon 64 deflated, sheath 20 may be pulled back through hole H with no further enlargement of hole H or damage to the surrounding tissue. An appropriate closure or other treatment for hole H may be applied, via sheath 20 or another structure. Once through hole H, sheath 20 is retracted from the body along the path of entry.

While the disclosure has been illustrated and described in detail in the drawings and foregoing description, the same is to be considered as illustrative and not restrictive in character, it being understood that only selected embodiments have been shown and described and that all equivalents, changes, and modifications that come within the spirit of the disclosures as defined herein or by the following claims are desired to be protected. It will be understood that features described particularly with respect to one or more specific structures or embodiments may be incorporated into or otherwise used with other structures or embodiments as disclosed herein.

The following numbered clauses set out specific embodiments that may be useful in understanding the present invention:

1. An introducer sheath for insertion through the right atrial appendage into the pericardial cavity, comprising:
    an inner lubricious layer defining an internal lumen extending along a longitudinal axis of the sheath from a proximal end to a distal end of the sheath;
    an outer heat-settable layer surrounding the inner layer and extending from the proximal end to the distal end;
    a coil core fixed between the inner layer and the outer layer, the coil core extending through at least part of a proximal portion of the sheath and at least part of a medial curved portion of the sheath but not into a linear distal portion of the sheath which includes the distal end;
    wherein the linear distal portion has a circumference around the longitudinal axis, and includes an indented portion around the entire circumference, the indented portion having proximal and distal edges an outer diameter less than a maximum outer diameter of the linear distal portion, and further comprising a balloon in the indented portion, the balloon having a deflated condition in which the balloon does not extend past either of the edges or the maximum outer diameter of the linear distal portion and an inflated condition in which the balloon extends coaxially past the maximum outer diameter of the linear distal portion around the circumference of the linear distal portion, and wherein the balloon in the inflated condition has a surface facing proximally that is angled with respect to the longitudinal axis at an angle between and including 60 to 90 degrees.

2. The sheath of clause 1, wherein the internal lumen has a constant inner diameter through the proximal, medial and distal portions of the sheath.

3. The sheath of any of clauses 1-2, further comprising at least one marker that abuts the proximal edge of the indented portion, the marker being at least one of radiopaque and echogenic.

4. The sheath of any of clauses 1-3, wherein a tip of the linear distal portion has at least one marker that is adjacent a longitudinal opening of the internal lumen, the marker being at least one of radiopaque and echogenic.

5. The sheath of any of clauses 3-4, wherein the marker is proximal of a proximal-most part of the balloon.

6. The sheath of any of clauses 1-5, further comprising a fluid lumen that extends to an opening in the indented portion, whereby a fluid may be forced through to inflate the balloon and may be withdrawn to deflate the balloon.

7. The sheath of any of clauses 1-6, wherein the inner layer is formed of polytetrafluoroethylene (PTFE).

8. The sheath of any of clauses 1-7, wherein the outer layer is formed of PEBAX and heat-set to a desired shape following attachment of the inner and outer layers to each other.

9. A method of accessing a pericardial cavity of a patient via a right atrial appendage of the patient with an introducer sheath, comprising:
    inserting the introducer sheath into the inferior vena cava of the patient, the introducer sheath having a curved medial portion and a linear distal portion, the linear distal portion including an indented portion around the entire circumference and a balloon in a deflated condition within the indented portion so that no part of the balloon extends beyond a maximum outer diameter of the linear distal portion or outside of the indented portion;
    moving the introducer sheath to the right atrium of the heart of the patient to a position adjacent the right atrial appendage;
    passing the sheath through the right atrial appendage to the pericardial cavity so that the indented portion is within the pericardial cavity;

inflating the balloon within the pericardial cavity, wherein the inflating does not enlarge a hole through the right atrial appendage through which the sheath passes; and engaging the balloon with tissue of the right atrial appendage that faces the pericardial cavity.

10. The method of clause 9, wherein the introducer sheath is the introducer sheath of claim 1.

11. The method of any of clauses 9-10, further comprising imaging the sheath when the sheath extends through the right atrial appendage, and confirming that a marker abutting a proximal edge of the indented section is beyond the tissue of the right atrial appendage before performing the inflating step.

12. The method of any of clauses 9-11, wherein a dilator is within and extending from the sheath, and the passing step includes dilating a hole through the right atrial appendage with the dilator.

13. The method of any of clauses 9-12, further comprising passing one or more devices through the sheath and into the pericardial cavity for use in a treatment procedure after said engaging step, and while the balloon is inflated and engaged with tissue of the right atrial appendage.

14. The method of clause 13, wherein the one or more devices includes a belt for placement in the atrioventricular groove as a treatment for tricuspid valve regurgitation.

15. The method of any of clauses 9-14, further comprising deflating the balloon so that the balloon collapses to a condition within the indented portion so that no part of the balloon extends beyond a maximum outer diameter of the linear distal portion or outside of the indented portion.

16. The method of clause 15, further comprising a disengaging step between the engaging and deflating step, wherein the disengaging step includes moving the sheath with respect to the right atrial appendage to move the balloon away from tissue of the right atrial appendage that faces the pericardial cavity.

The invention claimed is:

1. An introducer sheath for insertion through the right atrial appendage into the pericardial cavity, comprising:
    an inner lubricious layer defining an internal lumen extending along a longitudinal axis of the sheath from a proximal end to a distal end of the sheath;
    an outer heat-settable layer surrounding the inner layer and extending from the proximal end to the distal end;
    a coil core fixed between the inner layer and the outer layer, the coil core extending through at least part of a proximal portion of the sheath and at least part of a medial curved portion of the sheath but not into a linear distal portion of the sheath which includes the distal end;
    wherein the linear distal portion has a circumference around the longitudinal axis, and includes an indented portion around the entire circumference, the indented portion having proximal and distal edges an outer diameter less than a maximum outer diameter of the linear distal portion, and further comprising a balloon in the indented portion, the balloon having a deflated condition in which the balloon does not extend past either of the edges or the maximum outer diameter of the linear distal portion and an inflated condition in which the balloon extends coaxially past the maximum outer diameter of the linear distal portion around the circumference of the linear distal portion, and wherein the balloon in the inflated condition has a surface facing proximally that is angled with respect to the longitudinal axis at an angle between and including 60 to 90 degrees.

2. The sheath of claim 1, wherein the internal lumen has a constant inner diameter through the proximal, medial and distal portions of the sheath.

3. The sheath of claim 1, further comprising at least one marker that abuts the proximal edge of the indented portion, the marker being at least one of radiopaque and echogenic.

4. The sheath of claim 1, wherein a tip of the linear distal portion has at least one marker that is adjacent a longitudinal opening of the internal lumen, the marker being at least one of radiopaque and echogenic.

5. The sheath of claim 3, wherein the marker is proximal of a proximal-most part of the balloon.

6. The sheath of claim 1, further comprising a fluid lumen that extends to an opening in the indented portion, whereby a fluid may be forced through to inflate the balloon and may be withdrawn to deflate the balloon.

7. The sheath of claim 1, wherein the inner layer is formed of polytetrafluoroethylene (PTFE).

8. The sheath of claim 1, wherein the outer layer is formed of PEBAX and heat-set to a desired shape following attachment of the inner and outer layers to each other.

9. The sheath of claim 1, wherein the medial curved portion has a concave side that defines a concave curvature that extends around 20 to 40 degrees of arc.

10. The sheath of claim 1, wherein said angle is between or including 75 to 90 degrees.

11. The sheath of claim 1, wherein the distal end of the sheath is 6 mm or less from the indented portion.

12. The sheath of claim 1, in combination with a dilator receivable through the internal lumen, the dilator having a tapered distal end.

* * * * *

UNITED STATES PATENT AND TRADEMARK OFFICE
CERTIFICATE OF CORRECTION

PATENT NO. : 11,071,535 B2  
APPLICATION NO. : 16/394182  
DATED : July 27, 2021  
INVENTOR(S) : Shaun Davis Gittard et al.

Page 1 of 1

It is certified that error appears in the above-identified patent and that said Letters Patent is hereby corrected as shown below:

In the Specification

Column 1, Line 22, replace "arc" with --are--  
Column 1, Line 24, replace "he" with --be--  
Column 5, Line 12, replace "torquing" with --torqueing--  
Column 9, Line 48, replace "hack" with --back--  
Column 10, Line 11, replace "hut" with --but--

Signed and Sealed this  
Fifteenth Day of February, 2022

Drew Hirshfeld  
*Performing the Functions and Duties of the*  
*Under Secretary of Commerce for Intellectual Property and*  
*Director of the United States Patent and Trademark Office*